(12) United States Patent
Prost et al.

(10) Patent No.: US 7,935,672 B2
(45) Date of Patent: May 3, 2011

(54) DERIVATIVES OF GENKWANIN AND SAKURANETIN, COSMETIC AND THERAPEUTIC USE THEREOF AND PREPARATION METHOD OF SAME

(76) Inventors: Michel Prost, Couternon (FR); Jacqueline Ragot, Toulouse (FR); Pierre Tubery, Lamasquère (FR)

( * ) Notice: Subject to any disclaimer, the term of this patent is extended or adjusted under 35 U.S.C. 154(b) by 980 days.

(21) Appl. No.: 10/598,752

(22) PCT Filed: Mar. 11, 2005

(86) PCT No.: PCT/FR2005/000596
§ 371 (c)(1),
(2), (4) Date: May 29, 2007

(87) PCT Pub. No.: WO2005/087786
PCT Pub. Date: Sep. 22, 2005

(65) Prior Publication Data
US 2007/0299018 A1    Dec. 27, 2007

(30) Foreign Application Priority Data

Mar. 11, 2004    (FR) ..................... 04 02554

(51) Int. Cl.
*A61K 31/7028*    (2006.01)
*A61K 31/7042*    (2006.01)
*A61K 31/70*    (2006.01)
*C07H 17/07*    (2006.01)

(52) U.S. Cl. ............... 514/27; 514/25; 536/8; 536/18.1; 536/18.5; 536/4.1

(58) Field of Classification Search .................... 514/27, 514/25; 536/18.1, 18.5, 4.1, 8
See application file for complete search history.

(56) References Cited

FOREIGN PATENT DOCUMENTS

| EP | 0 633 022 A | | 1/1995 |
|---|---|---|---|
| EP | 0633022 A | * | 1/1995 |
| FR | 2 597 751 A | | 10/1987 |
| WO | WO 85/05031 | * | 10/1985 |
| WO | WO 03/031430 A | | 4/2003 |

OTHER PUBLICATIONS

Trisha Gura; Science vol. 278; Nov. 7, 1997, 1041-1042.*
Deiana M. et al: "Chemical composition and antioxidant activity of extracts from *Daphne gnidium* L" Journal of the american oil chemists' society. american oil chemists' society. Champaign, US vol. 80, No. 1, 2003, pp. 65-70, XP001183469 ISSN:0003-021X.
International Search Report PCT/FR2005/000596 dated Jun. 7, 2005 (European Patent Office, The Netherlands).

* cited by examiner

*Primary Examiner* — Shaojia Anna Jiang
*Assistant Examiner* — Michael C Henry
(74) *Attorney, Agent, or Firm* — Ostrolenk Faber LLP

(57) ABSTRACT

The invention relates to: (i) the use of osyl derivatives of genkwanin and sakuranetin having formula (I) in (a) cosmetics or dermatology and (b) therapeutics; (ii) the use of novel derivatives having formula (I) as industrial products; and (iii) the production method thereof [Formula (I)], wherein symbol [Formula (II)] represents a single or double bond, R represents H or an osyl residue, particularly with structure $S^1$ or $s^2$ [Formula (III)], Z represents H, an alkyl group at $C_1$-$C_4$, acyl at $C_1$-$C_5$, monosaccharide or sulphate.

4 Claims, 2 Drawing Sheets

Fig. 2
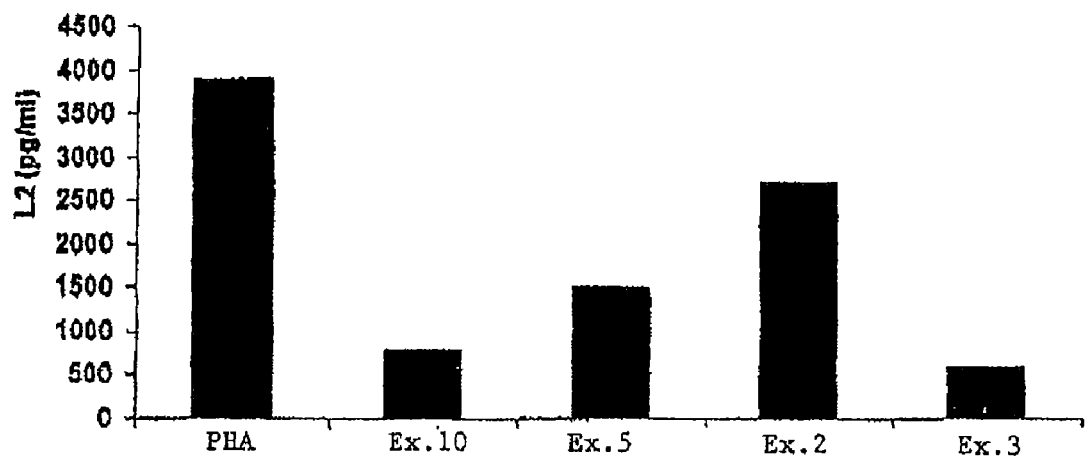
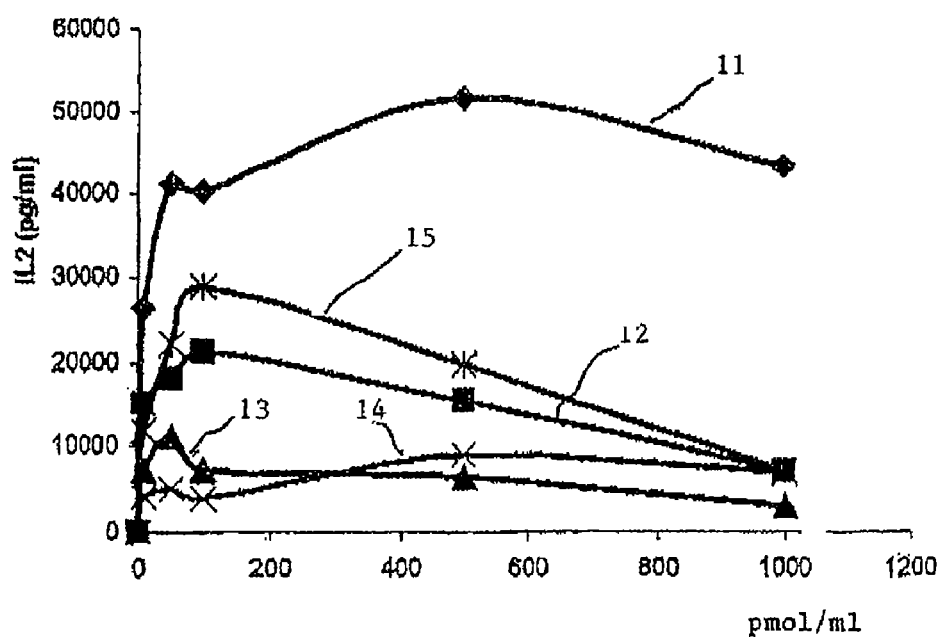
Fig. 3

DERIVATIVES OF GENKWANIN AND SAKURANETIN, COSMETIC AND THERAPEUTIC USE THEREOF AND PREPARATION METHOD OF SAME

CROSS REFERENCE TO RELATED APPLICATIONS

The present application is a 35 U.S.C. §371 National Phase conversion of PCT/FR2005/000596 filed March 11, 2005, which claims priority of French Application No. 0402554 filed Mar. 11, 2004. The PCT International Application was published in the French language.

FIELD OF THE INVENTION

The present invention relates to saccharide derivatives of genkwanin and sakuranetin. More specifically, it relates to (i) the cosmetic or dermatological use, on the one hand, and the therapeutic use, on the other hand, of saccharide derivatives of genkwanin and sakuranetin of formula I below, (ii) novel derivatives of formula I as industrial products, and (iii) the manufacturing process therefor.

The compounds according to the invention correspond to formula I:

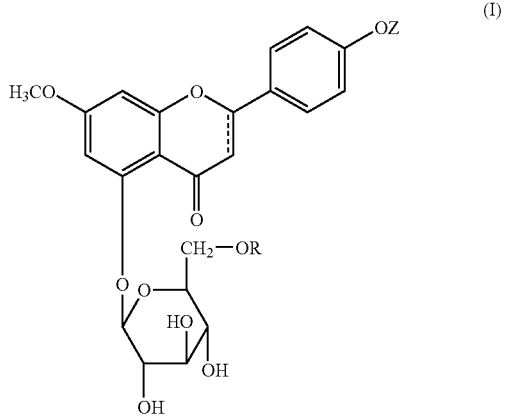

(I)

in which,
the symbol ≡≡≡ represents a single or double bond,
R represents H or a saccharide residue, especially of structure $S^1$ or $S^2$:

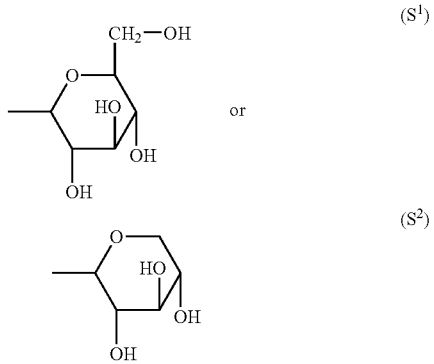

(S¹)

(S²)

Z represents H or a $C_1$-$C_4$ alkyl, $C_1$-$C_5$ acyl, saccharide or sulfate group.

BACKGROUND OF THE INVENTION

It is known that a number of products of formula I have already been described and studied in the past. In particular, 5-O-β-D-primeverosyl-genkwanin (which is a compound of formula I in which the symbol ≡≡≡ represents a double bond, R is a saccharide residue of structure $S^2$ and Z is H) is obtained by extraction of *Gnidia kraussiana* (a plant from the African savanna of the Thymeleacea family) and has immune (especially immunostimulatory), anticancer and antileukemic properties. More specifically, during serious immune disorders, the physiological lymphoblasts are in hyperplasia, and the value of 5-O-β-D-primeverosyl-genkwanin lies in the fact that it destroys the lymphoblasts formed. See in this respect FR 2 510 580 A, FR 2 597 751 A and the article by Jer-Huei LIN et al., *Yaowu Shipin Fenxi,* 2001; 9(1), 6-11.

Pinostrobin-5-glucoside (which is a compound of formula I in which the symbol ≡≡≡ represents a double bond, R is H and Z is H) was isolated from the bark of *Prunus cerasus* and is considered as being characteristic of the species *Prunus cerasus*. See in this respect the article by Martin Geibel et al., *Phythochemistry,* 1991; 30(5), 1519-1521.

Sakuranin, other nomenclature: sakuranetin-5-glucoside (which is a compound of formula I in which the symbol ≡≡≡ represents a single bond, R is H and Z is H) was isolated from *Prunus yedoensis*, without its possible cosmetic or pharmacological properties (especially the free-radical-scavenging properties) being studied. See in this respect the publication *Merck Index,* 12th Edition, 1996, *Monograph No.* 8470, pages 1431-1432.

The abovementioned prior art does not describe or suggest that the compounds of formula I according to the invention have beneficial properties:
in cosmetics or dermatopharmaceutics, as substances for improving the texture of the skin, and
in human or veterinary therapy (especially warm-blooded animals), as free-radical scavengers.

SUMMARY OF THE INVENTION

According to a first aspect of the invention, a novel use of saccharide derivatives of genkwanin and sakuranetin is recommended, as (a) cosmetic or dermatological substances, or (b) free-radical-scavenging substances, for (a) improving the texture of the skin or, respectively, (b) treating or preventing disorders caused by free radicals.

In this regard, a novel use (a) in cosmetics or dermatology, on the one hand, or (b) in human or veterinary therapy, on the other hand, is provided, said use being characterized in that use is made of a substance chosen from the group consisting of
(i) saccharide derivatives of genkwanin or sakuranetin of formula I:

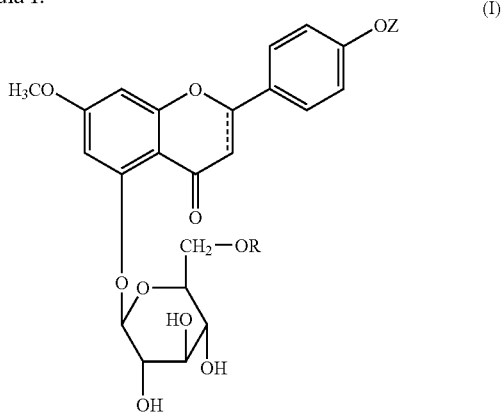

(I)

in which:

the symbol ⚌ represents a single or double bond,

R represents H or a saccharide residue, especially of structure $S^1$ or $S^2$:

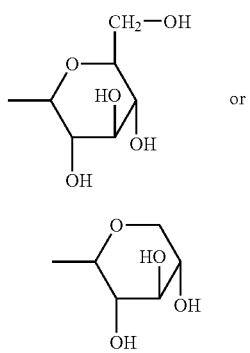

Z represents H or a $C_1$-$C_4$ alkyl, $C_1$-$C_5$ acyl, saccharide or sulfate group, and (ii) mixtures thereof, as (a) a cosmetic or dermatological active ingredient or, respectively, (b) a free-radical-scavenging active ingredient, for obtaining (a) a cosmetic or dermatological preparation for improving the texture of the skin or, respectively, (b) a medicament for therapeutic use against disorders caused by free radicals.

According to a second aspect of the invention, compounds of formula I in which R is especially a saccharide residue of structure $S^1$, and mixtures thereof, are recommended as novel industrial products.

According to a third aspect of the invention, a process for preparing compounds of formula I and in particular for the preparation of said novel compounds is recommended.

BRIEF DESCRIPTION OF THE DRAWINGS

The attached figures concern some of the results of the tests undertaken with products of formula I:

FIGS. 2 and 3 show that the products of formula I tested are of value as immunosuppressants.

DETAILED DESCRIPTION OF THE INVENTION

Figure 1:
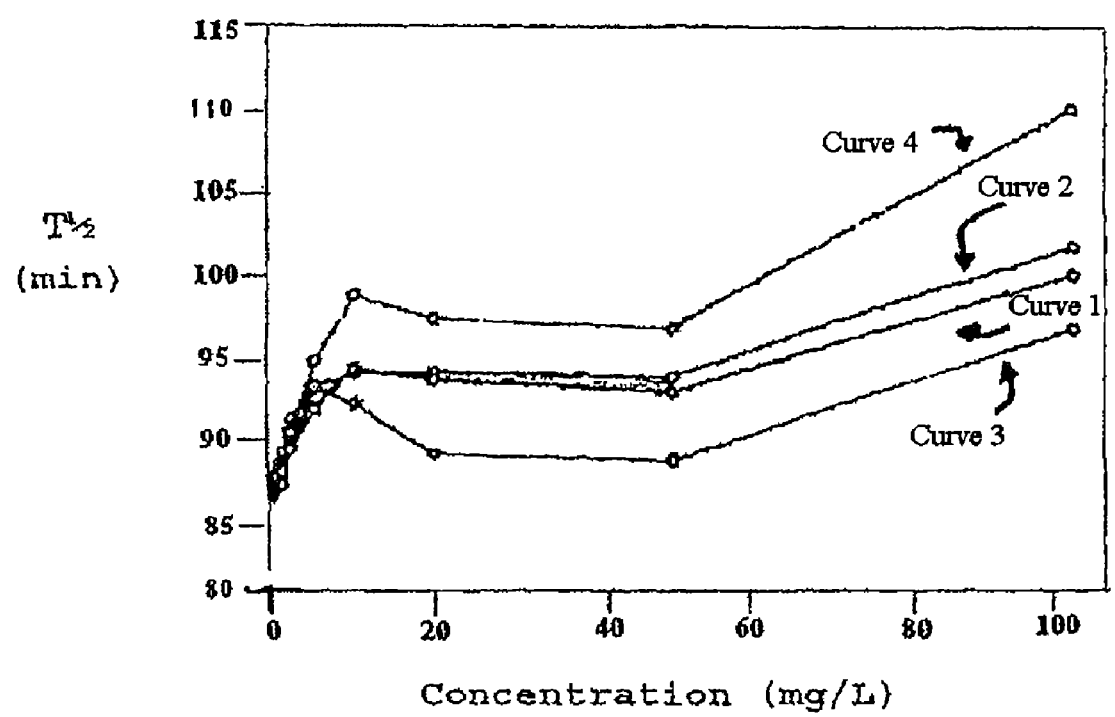
FIG. 1 shows that the products of formula I tested have free-radical-scavenging properties.

The present invention covers saccharide derivatives of genkwanin when the symbol ⚌ represents a double bond, on the one hand, and saccharide derivatives of sakuranetin when said symbol ⚌ represents a single bond, on the other hand.

In the definition of Z, the $C_1$-$C_4$ alkyl groups comprise linear or branched groups with a hydrocarbon-based chain, i.e. methyl, ethyl, n-propyl, isopropyl, n-butyl, sec-butyl and tert-butyl groups; the $C_1$-$C_5$ acyl groups comprise linear or branched aliphatic groups with a hydrocarbon-based chain, containing from 1 to 5 carbon atoms, i.e. $CH_3CO$, $CH_3CH_2CO$, $CH_3CH_2CH_2CO$, $(CH_3)_2CHCO$, $CH_3CH_2CH_2CH_2CO$, $(CH_3)_2CHCH_2CO$, $CH_3CH_2CH(CH_3)CO$ and $(CH_3)_3CCO$ groups; the sulfate group comprises the residue $SO_3^-$, which is mainly encountered in the acid form $SO_3H$ and, where appropriate, in a salified form such as $SO_3NH_4$ or $SO_3Na$. Finally, the group Z may represent a saccharide residue, especially a glucosyl, xylosyl, thioxylosyl, fructosyl, mannosyl, etc. residue.

The saccharide group included in the definition of R may be any saccharide residue, especially one of the residues listed above for the group for Z. Advantageously, the groups R according to the invention will be of structure $S^1$ or $S^2$, the structure $S^1$ being preferred.

Among the compounds of formula I in accordance with the invention, mention may be made advantageously of:

5-[O-6-(D-glucopyranosyl)-β-D-glucopyranosyl]oxy-2-(4-ethoxyphenyl)-7-methoxy-4H-1-benzopyran-4-one [other nomenclature: 4'-ethoxy-genkwanin-5-(D-glucosido)-β-D-glucoside] of formula Ia:

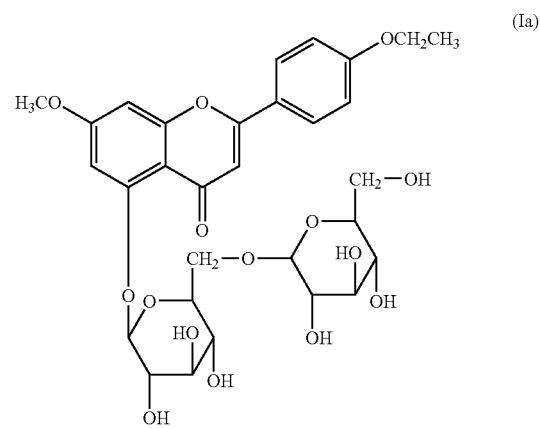

which is the most advantageous product of the invention;

the abovementioned 5-O-β-D-primeverosyl-genkwanin of formula IIa:

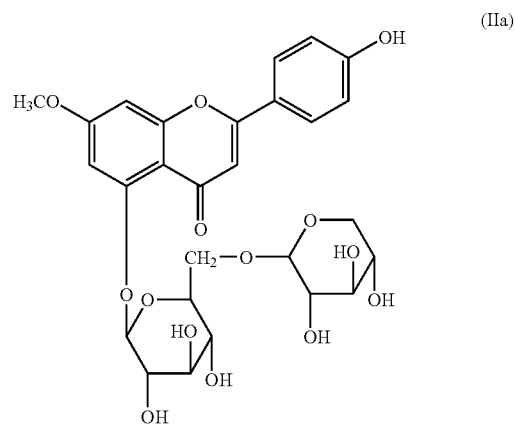

the abovementioned pinostrobin-5-glucoside of formula IIIa:

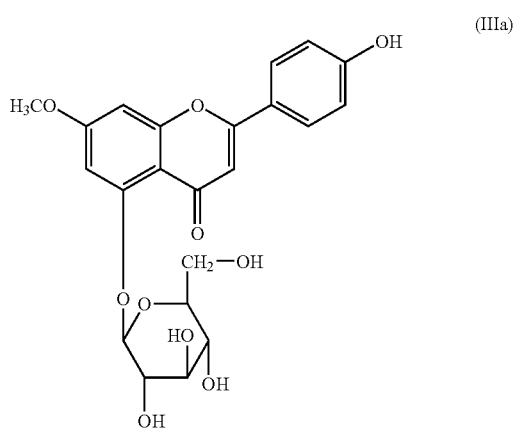

2,3-dihydro-5-[O-6-(D-gluocpyranosyl)-β-D-glucopyranosyl]oxy-2-(4-ethoxyphenyl)-7-methoxy-4H-1-benzopyran-4-one [other nomenclature: 4'-ethoxysakuranetin-5-(D-glucoside)-β-D-glucoside of formula Ib:

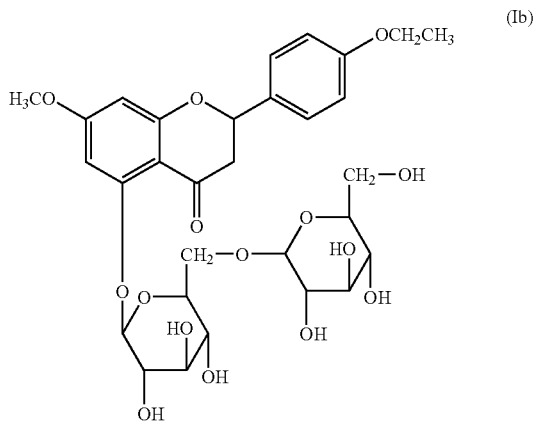

(Ib)

which is the homolog of the product of formula Ia with regard to the replacement of genkwanin with sakuranetin, 5-O-β-D-primeverosyl-sakuranetin of formula IIb:

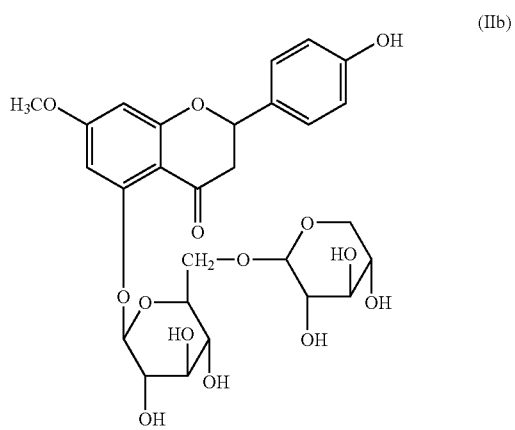

(IIb)

and derivatives thereof in which Z is a sulfate group (preferably $SO_3H$ or, where appropriate, $SO_3Na$ or even $SO_3NH_4$).

Among the novel compounds according to the invention, mention may be made more particularly of the products of formula IV:

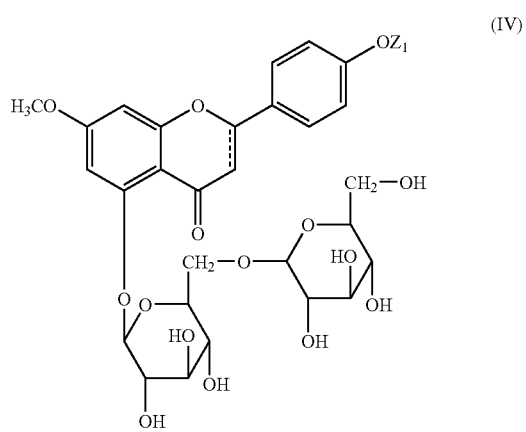

(IV)

in which the symbol ═══ represents a single or double bond and $Z_1$ has the same definition as Z above and advantageously represents a $C_1$-$C_4$ alkyl group (preferably an ethyl group) or a sulfate group (preferably an $SO_3H$ group).

The compounds of formula I may be prepared according to a method that is known per se by application of standard reaction mechanisms and/or extraction processes. By way of example: (i) genkwanin, sakuranetin or a saccharide thereof are extracted from a suitable plant belonging to the set: *Prunus, Gnidia* and *Daphne*; (ii) the aglycone is osylated in position 5 with a suitable saccharide (if necessary after blocking the OH function in position 4' if it is not protected); and/or (iii) the 4'—OH group of the saccharide extracted or prepared as indicated above (if necessary after deprotection of the 4'—OH group) is etherified (especially using an alkyl iodide so as not to affect the OH groups of the sugar portion), esterified or sulfated.

The process that is recommended according to the invention for preparing the compound of formula Ia is characterized in that it comprises the steps consisting in:

(1°) extracting the ground roots of *Daphne gnidium* with $CH_2Cl_2$;

(2°) filtering to discard the methylene chloride solution thus obtained, and collecting the solid residue, which is dried;

(3°) extracting said dry solid residue thus obtained with $CH_3OH$;

(4°) filtering to collect the methanol solution thus obtained, and discarding the resulting solid residue;

(5°) evaporating to dryness the methanol solution thus collected, under vacuum, at a temperature of less than or equal to 60° C., to obtain a solid residue;

(6°) washing the solid residue thus obtained in step (5°), with water at a temperature of less than or equal to 60° C. with stirring, and leaving to cool;

(7°) removing the washing water and then taking up the solid residue with $CH_3OH$;

(8°) repeating the cycle of operations of steps (5°) to (7°) 3 to 7 times until the final washing water is pale yellow and clear;

(9°) taking up the resulting dry residue in a 25/2 w/w methanol/water mixture in an amount that is suitable to obtain a liquid with a density of 0.885 g/mL;

(10°) leaving said liquid to stand at 2-4° C. and preferably at 3° C., for at least 2 days and preferably for 3 days, and collecting the precipitate formed;

(11°) washing said precipitate successively with methanol and then methanol/ether mixtures with increasing ether contents, until the supernatant is colorless;

(12°) filtering off the precipitate thus obtained, and washing it several times with ether, until the washing ether is colorless;

(13°) filtering off and drying the resulting solid product, which consists of a mixture of the products of formulae Ia, IIa and IIIa; and (14°) if necessary, separating said mixture to collect the product of formula Ia.

In practice, the extraction step (1°) is performed under warm conditions (i.e. at a temperature of 30-35° C. at atmospheric pressure (~$10^5$ Pa) or, where appropriate, at a higher temperature under reduced pressure) for 3-6 days (preferably for 5 days) in apparatus of Kumagawa type; the extraction in step (3°) is performed under warm conditions (especially at a temperature of 45-55° C. at normal pressure (≈$10^5$ Pa) or, where appropriate, at a higher temperature under reduced pressure) in the same apparatus for 3-6 days (preferably for 5 days).

As regards the abovementioned preferential modes, a mixture Ia/IIa/IIIa in a weight ratio of about 10/85/5 w/w is obtained after step (13°).

As a function of the purifications undertaken by chromatography, the following is obtained after step (14°):

a mixture Ia/IIa enriched in Ia, especially an 80/20 w/w Ia/IIa mixture, or the essentially pure compound of formula Ia (i.e. in a purity of greater than or equal to 98%) or the more purified compound of formula Ia (i.e. in a purity of greater than or equal to 99.5%).

The compounds of formula I, and in particular the novel compounds of formula IV, are useful in cosmetics or dermopharmaceutics as agents for improving the texture of the skin.

When administered topically, in the form of a solution, a lotion, a gel or an emulsion, which may be a multiple emulsion (for example an O/L/O or L/O/L emulsion), the compounds of formula I or IV have:

a favorable action on the effects of ageing of the skin, especially for reducing wrinkles and giving the skin the desired firmness and suppleness;

an anti-ageing effect that allows the injection of collagen to be avoided; and power in controlling the moisturization of the skin.

In particular, since the compounds of formula I or, respectively, IV become readily hydrated to I.$xH_2O$ or, respectively, IV.$xH_2O$ (in which x is an integer or fraction especially between 0.3 and 5), they serve, according to the invention, in the thickness of the skin as moisturization regulators, either by taking up the excess water, or especially by providing water when the water content in the skin is insufficient.

Besides the abovementioned cosmetic or dermatological aspect, the compounds of formula I or IV are useful in human or veterinary therapy on account of their free-radical-scavenging properties, for treating and especially preventing disorders induced by free radicals.

Said disorders in particular include pathologies induced by an overproduction or uncontrolled production of free radicals in the body, such as myelodegenerative diseases, manic-depressive syndrome and senile dementia. The compounds of formula I or IV are above all advantageous in human therapy before these pathologies become irreversible.

Moreover, all the compounds of formula IV that were tested with regard to their immunomodulatory, antiatheroma and anticancer properties proved to be effective. The preferred substance according to the invention, which consists of the product of formula Ia or the abovementioned mixtures Ia/IIa/IIIa (i.e. extract of *Daphne gnidium*) and Ia/IIa, is particularly active against certain acute cancers and leukemias (antiblastic effect, i.e. destruction of leukoblasts) and chronic myeloid leukemia.

According to the invention, a cosmetic (a), dermatopharmaceutical (b) or therapeutic (c) composition is recommended, which is characterized in that:

(a) the cosmetic composition contains, in combination with a physiologically acceptable topical excipient, at least one compound of formula I;

(b) the dermatopharmaceutical composition contains, in combination with a physiologically acceptable and especially topical excipient, at least one compound of formula I; or (c) the therapeutic composition contains, in combination with a physiologically acceptable and especially oral or injectable excipient, at least one compound of formula IV as immunomodulatory active ingredient, especially against recent bouts of multiple sclerosis, or an anticancer active ingredient, especially against chronic myeloid leukemia.

Other advantages and characteristics of the invention will be understood more clearly on reading the preparation examples and the results of cosmetological and pharmacological tests below. Needless to say, these data are in no way limiting, but provided for the purpose of illustration.

EXAMPLES

The following examples are provided only for the purpose of illustrating the invention and are not to be construed as limiting the invention in any manner.

A few typical compounds of formula I have been collated in table I below with comparative products (CP.1 and CP.2).

TABLE I

| Typical compounds according to the invention | |
|---|---|
| Example | Structure |
| Ex. 1 | 10/85/5 w/w Ia/IIa/IIIa mixture |
| Ex. 2 | Product of formula IIa |
| Ex. 3 | Product of formula IIIa |
| Ex. 4 | 80/20 w/w Ia/IIa mixture |
| Ex. 5 | Product of formula Ib |
| Ex. 6 | Product of formula IIb |
| Ex. 7 | 4'-sulfate of the product of formula Ib |
| Ex. 8 | Product of formula Ia |
| Ex. 9 | 4'-sulfate of the product of formula Ia |
| Ex. 10 | 10/85/5 w/w Ib/IIa/IIIa mixture |
| CP. 1 | Genkwanin |
| CP. 2 | Sakuranetin |

Preparation A

-Production of the 10/85/5 w/w Ia/IIa/IIIa Mixture (Ex. 1)-

11 kg of Daphne gnidium roots (plant from the Mediterranean basin of the Thymeleacea family) are ground and then treated continuously with methylene chloride, at 30-35° C., for 5 days in apparatus of Kumagawa type. The liquid solution thus obtained is discarded and the solid residue is collected and dried. Said residue thus dried is extracted with hot methanol (45-55° C.) for 5 days in said apparatus of Kumagawa type. The methanolic extract, obtained after discarding the solid residue, is treated in the following manner: evaporation to dryness under reduced pressure at a temperature below 60° C. in a round-bottomed flask; washing of the solid residue thus obtained with hot water while shaking so as to detach said residue from the bottom of the flask; cooling to room temperature and removal of the washing water; and uptake of the residue in methanol. This succession of treatments is repeated 5 to 7 times, depending on the origin of the roots, until the final washing water is clear and pale yellow. The resulting residue is taken up in warm methanol (45-55° C.) containing 8% by weight of water, in an amount sufficient to obtain a liquid with a density of 0.885 g/mL. The resulting solution is left to stand for 3 days at 3° C. and the precipitate formed is then recovered by centrifugation. This precipitate is washed with successive fractions of methanol and then of methanol/dimethyl ether (or methanol/diethyl ether) mixtures increasingly rich in ether. When the supernatant is finally virtually colorless, the precipitate is filtered off and washed several times with ether until the washing ether is colorless. A very pale beige-colored solid is obtained, and is dried under reduced pressure and then ground.

This solid is a Ia/IIa/IIIa mixture in a 10/85/5 weight ratio. The yield is about 2 to 3% depending on the origin of the plant and the season during which the roots were harvested.

Analysis

Since the compounds of formulae Ia, IIa and IIIa are of similar structure (flavonoid part and saccharide part), they have strong spectroscopic similarities, in particular in the ultraviolet and infrared regions.

UV spectrum (in 80/20 v/v acetonitrile/water mixture)

Two absorption bands at 331.7 and 261.7 nanometers are observed (the band at 261.7 nm having an intensity that is about half that of the band at 331.7 nm).

IR spectra (in KBr disk)

The following bands are observed:
strong band at 3374 cm$^{-1}$ (O—H of the sugar part);
strong band at 1635 cm$^{-1}$ (vibration band of the flavone carbonyl);
medium-strength band at 1609 cm$^{-1}$ (vibration band of the flavone ethylenic double bond); and
medium-strength bands at 1450 and 1360 cm$^{-1}$ (vibration bands of the aromatic parts).

Preparation B

-Production of the 80/20 w/w Ia/IIa Mixture (Ex. 4)-

By subjecting the product of example 1 to separative chromatography (HPLC), the 80/20 w/w Ia/IIa mixture is obtained.

Preparation C

-Production of the Product of Formula Ia (Ex. 8)-

By subjecting the product of example 1 or of example 4 to a more rigorous separative chromatography, the compound of formula Ia is obtained in a purity of greater than or equal to 98%, or even in a purity of greater than or equal to 99.5%.

Analysis

The NMR spectra (at 250 Mhz as a solution in deuterated methanol) and the mass spectrum (via the FAB technique) were determined. The results obtained are as follows, in which the first sugar unit is that attached to the flavone backbone and the 2nd sugar unit is that of structure S$^1$ or S$^2$.

NMR Spectrum
triplet centered at 1.31 ppm (methyl group CH$_3$ of the alkylenated phenyl chain);
quadrate centered at 3.20 ppm (methanol group CH$_2$ of said alkyl chain);
unresolved band from 3.27 to 4.39 ppm (protons of the two sugar units) [detailed assignments on the basis of COSY, HMQC and HMBC experiments at 600 Mhz, the two anomeric protons of the two sugar units of which, at, respectively, 4.75 ppm (doublet) for the 1st unit attached to the flavone at position 5, and 4.27 ppm (doublet) for the 2nd unit; —CH$_2$—O— bridge between the two sugar units at 3.60 (d) and 3.93 (d) ppm; and —CH$_2$— at 5 on the 2nd sugar unit at 3.32 (d) and 3.60 (d) ppm; the stereochemistry of the two sugar units having been established on the basis of vicinal proton-proton couplings starting from the anomeric protons];
3.87 ppm (CH$_3$ of the CH$_3$—O— group);
6.60 ppm (ethylenic proton of the flavone part);
unresolved band at 6.91-6.94 ppm (4 aromatic protons); and
unresolved band at 7.82-7.86 ppm (2 aromatic protons).

Mass Spectrum
Molecular mass: 636.598 (C$_{30}$H$_{36}$O$_{15}$)
Mass peak: 636; Na and K adducts in compliance.

The mass spectrometry method was also used to confirm the structures of formulae Ia, IIa and IIIa after acetylation of all the O—H groups (with acetic anhydride/pyridine mixture); the acetylation products were analyzed by mass spectrometry after chromatographic purification on silica (eluent: 50/50 v/v water/acetonitrile).

Preparation C a

-Production of the Products of Formula IIa (Ex. 2) and of Formula IIIa (Ex. 3)-

By subjecting the product of example 1 to more rigorous separative chromatographies, the products of formula IIa (Ex. 2) and of formula IIIa (Ex. 3) were isolated in a purity of greater than or equal to 98%.

Analysis (Performed as Indicated in Preparation C Above)

NMR spectrum of Ex. 2

The NMR spectrum of the product of formula IIa (Ex. 2) is identical to that of the product of formula Ia (Ex. 8), but with the following differences:
absence of CH$_3$ signal at 1.31 ppm and of CH$_2$ signal at 3.20 ppm for the ethyl chain;
disappearance of the signals at 3.32 and 3.60 ppm for the CH$_2$ in position 5 on the second sugar.

Mass spectrum of Ex. 2
Molecular mass: 578.519 (C$_{27}$H$_{30}$O$_{14}$)
Mass peak: 578; Na and K adducts in compliance.

NMR spectrum of Ex. 3
The NMR spectrum of the product of formula IIIa (Ex. 3) is identical to that of the product of formula Ia (Ex. 8), but with the following difference:
simplification of the unresolved band corresponding to the protons of the sugar part, with only one anomeric proton at 4.76 ppm (d).

Mass spectrum of Ex. 3
Molecular mass: 446.404 (C$_{22}$H$_{22}$O$_{10}$)
Mass peak: 446; Na and K adducts in compliance.

Preparation D

-Production of the Product of Formula Ib (Ex. 5)-

By repeating the process of Preparations A and C above, starting with the bark or roots of *Prunus yedoensis*, the compound of formula Ib is obtained.

Preparation E

-Production of the 4'-Sulfate of the Product of Formula Ib (Ex. 7)-

The expected product is obtained by sulfatation of the 4'—OH group according to a method that is known per se.

Tests F

The capacity for improving the texture of the skin was evaluated by means of regenerating skin tissue after burning.

A portion of the back of adult male rats is shaved and a 0.5 cm$^2$ metal plate heated to a temperature of 130° C. is applied to this portion to create a calibrated burn area. A gel containing 0 (control batch) or 1.5% by weight of product of formula I (treated batches) is applied once a day for 21 days to the rats' burn (8 animals per test product, 10 animals for the control batch). It is found that, in the treated batches (Ex. 1 to Ex. 10), regeneration of the skin tissue is obtained in 1 month; on the other hand, in the control batch, said regeneration takes place in 6 to 8 weeks.

Tests G

The free-radical-scavenging properties of the products according to the invention (Ex. 1 to Ex. 10) were studied according to the "determination of the free-radical defense potential") process, which is the subject of French patent application No. 03 12 351 filed on 22 Oct. 2003, by monitoring the kinetics of erythrocyte lysis (especially of sheep erythrocytes; it is also possible to work on whole blood or blood plasma) induced by free radicals generated in situ, in the presence of a product according to the invention at doses increasing from 0 mg/L (control batch) to 100 mg/L (treated batches), and with hydrolysis of the reaction medium using a mixture of enzymes (β-glucosidase, sulfatase and β-glucuronidase).

According to this process, the (T½) time, which corresponds to the lysis of half of the cells under consideration, in this case erythrocytes, as a function of the concentration (in mg/L) of the test product of formula I, is measured in particular.

Part of the results obtained are collated in FIG. 1 below, in which curve 1 is that for the product Ex. 1; curve 2 that for Ex. 2; curve 3, that for Ex. 3; and curve 4, that for Ex. 4.

FIG. 1 shows that Ex. 4 (i.e. the 80/20 w/w Ia/IIa mixture), which contains compound Ia (i.e. Ex. 8) "contaminated" with compound IIa (i.e. Ex. 2), is more active as a free-radical-scavenging substance than Ex. 1, Ex. 2 and Ex. 3.

Tests H

Additional tests were performed with Ex. 10 and the constituents thereof (Ex. 5, Ex. 2 and Ex. 3) on human blood cells [supplied by EFS (Etablissements Francais du Sang)].

These are blood cells isolated on a Ficoll cushion and stored under liquid nitrogen vapor. After thawing, said cells are incubated for 24 hours at 37° C. before addition of the test products of formula I. After reincubation at 37° C. for 24 hours or 48 hours, the cells are analyzed to assess any expression of significant membrane markers, according to table II below.

TABLE II

| Analyses of the cell material | Expression of the membrane marker |
|---|---|
| T lymphocytes | CD3 |
| Cytotoxic T lymphocytes | CD8 |
| "Helper" T lymphocytes | CD4 |
| B lymphocytes | CD19 |
| Monocytes/macrophages | CD11c |
| Cell activations | CD69 |
| Cell supernatants | IL-2 |

As indicated in table II, the cell supernatants were analyzed for their interleukin 2 (IL-2) content, which is a product that induces T lymphocyte proliferation, with or without addition of an activator, especially (i) phytohematoglutinine (PHA), which is a standard activator, and (ii) a superantigen (SEB), which induces an interaction between class II B lymphocyte molecules with T lymphocyte receptors or TRC, thus mimicking an antigen presentation.

Two major points are observed, namely:
(1) Ex. 10 and its constituents, Ex. 5, Ex. 2 and Ex. 3 do not induce proliferation of the blood cells of the immune response; and
(2) Ex. 10, Ex. 5, Ex. 2 and Ex. 3 are active on these cells and interfere with the cascades of signals leading to an immune response; the effect observed appears to be immunosuppressant with a decrease in antibody production for the B lymphocytes, a decrease in class II MHCs for dendritic cells and an inhibition of IL-2 production (factor inducing lymphocyte proliferation) following stimulation with PHA or SEB.

FIGS. 2 and 3 show the effect of products Ex. 10, Ex. 5, Ex. 2 and Ex. 3 on the PHA-induced (FIG. 2) and, respectively, SEB-induced (FIG. 3) secretion of IL-2. In particular, FIG. 3, on the one hand, shows the production (expressed in pg/mL) of IL-2 relative to the concentration (expressed in pmol/mL) of SEB (curve 11), SEB+Ex. 10 (curve 12), SEB+Ex. 5 (curve 13), SEB+Ex. 2 (curve 14) and SEB+Ex. 3 (curve 15) and, on the other hand, shows the effect of products Ex. 10, Ex. 5, Ex. 2 and Ex. 3 on immune cell stimulation.

In conclusion, the compounds of formula IV, and especially the products of examples 1, 4, 8, 9 and 10, are particularly advantageous with regard to:

their immunomodulatory effects, especially with respect to recent bouts of multiple sclerosis;

their immunosuppressant effects, especially illustrated by inhibition of the activity of the stimulants PHA and SEB on IL-2 production;

their antiblastic effects (i.e. by destruction of leukoblasts) and which are useful in the treatment of chronic myeloid leukemia and acute leukemias;

their effects against certain cancers; and the virtual absence of harmful side effects when they are administered topically, orally or by injection.

In human adults, the recommended dosage for the products of formula I, and preferably the products of formula IV, is about 50 mg/kg per os. These products may also be administered locally in the form of gels or pomades; ointments or lotions; in this event, the local form may contain from 1% to 5% by weight of product of formula I, of formula IV or of a mixture thereof, relative to the weight of said local form.

What is claimed is:

1. An oside product of genkwanin, which is of the formula Io:

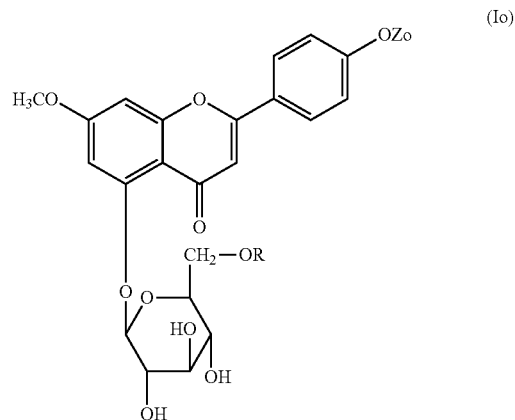

wherein R is H or an ose group of the structure $S^1$ or $S^2$:

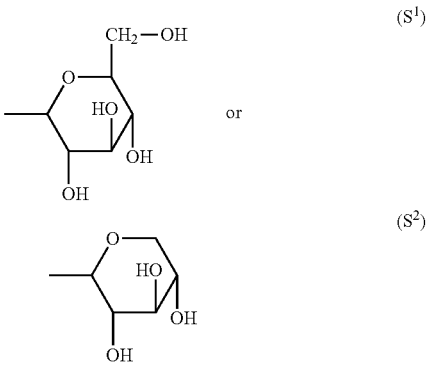

and Zo is H or $CH_2CH_3$, and selected from the group consisting of:

(i) 5-[O-6-(D-glucopyranosyl)-β-D-glucopyranosyl]oxy-2-(4-ethoxyxyphenyl)-7-methoxy-4H-1-benzopyran-4-one of the formula Ia:

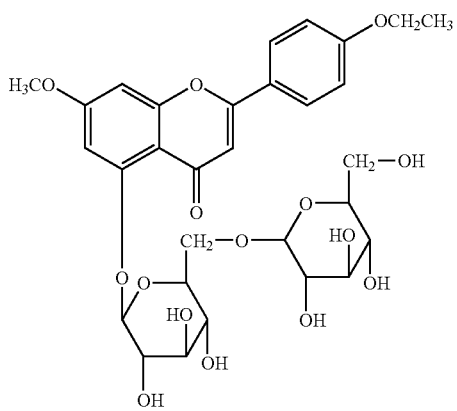

(Ia)

(ii) a mixture of said compound of the formula Ia with 5-O-β-D-primeverosyl-genkwanine of the formula IIa:

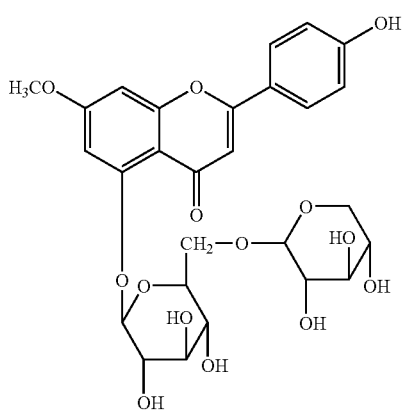

(IIa)

and pinostrobine-5-glucoside of the formula IIIa:

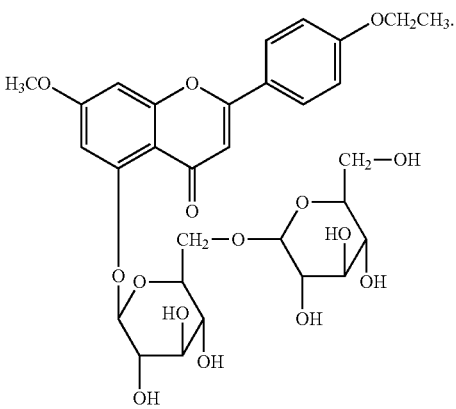

(IIIa)

wherein the Ia/IIa/IIIa weight ratio is of 10/85/5, and (iii) a mixture of said compound of the formula Ia with said 5-O-β-D-primeverosyl-genkwanine of the formula IIa, wherein the Ia/IIa weight ratio is of 80/20.

2. An oside product of genkwanin according to claim 1, which is 5-[O-6-(D-glucopyranosyl β-D-glucopyranosyl]oxy-2-(4-ethoxyxyphenyl)-7-methoxy-4H-1-benzopyran-4-one of the formula Ia:

(Ia)

3. An oside product of genkwanin according to claim 1, which is the Ia/IIa/IIIa 10/85/5 w/w mixture.

4. An oside product of genkwanin according to claim 1, which is the Ia/IIa 80/20 w/w mixture.

\* \* \* \* \*